(12) United States Patent
Dreher et al.

(10) Patent No.: US 7,832,863 B2
(45) Date of Patent: Nov. 16, 2010

(54) CUSTOMIZED Z-LENS DESIGN PROGRAM

(75) Inventors: Andreas W. Dreher, Escondido, CA (US); Bill Foote, San Diego, CA (US); Dave Sandler, San Diego, CA (US); Laurence Warden, Poway, CA (US)

(73) Assignee: Ophthonix, Inc., Vista, CA (US)

( * ) Notice: Subject to any disclaimer, the term of this patent is extended or adjusted under 35 U.S.C. 154(b) by 0 days.

(21) Appl. No.: 11/963,609

(22) Filed: Dec. 21, 2007

(65) Prior Publication Data

US 2009/0161071 A1 Jun. 25, 2009

(51) Int. Cl.
G02C 7/02 (2006.01)
(52) U.S. Cl. ..................................... 351/177; 351/159
(58) Field of Classification Search ................. 351/177, 351/204, 205, 246, 159, 176; 716/21
See application file for complete search history.

(56) References Cited

U.S. PATENT DOCUMENTS

| | | | |
|---|---|---|---|
| 6,511,180 | B2 | 1/2003 | Guirao et al. |
| 6,786,602 | B2 | 9/2004 | Abitbol |
| 6,786,603 | B2 | 9/2004 | Altmann |
| 7,331,674 | B2 * | 2/2008 | Dai .............................. 351/246 |
| 7,377,641 | B2 * | 5/2008 | Piers et al. .................... 351/177 |
| 2005/0024585 | A1 | 2/2005 | Dai |
| 2005/0057723 | A1 | 3/2005 | Wakil et al. |
| 2005/0195364 | A1 | 9/2005 | Dai |
| 2005/0231683 | A1 | 10/2005 | Ben-Zeev et al. |
| 2006/0023163 | A1 | 2/2006 | Foster |
| 2006/0139570 | A1 | 6/2006 | Blum et al. |
| 2006/0189966 | A1 | 8/2006 | Lieberman et al. |
| 2006/0203198 | A1 | 9/2006 | Liang |

OTHER PUBLICATIONS

International, Essilor, comp. Ophthalmic Optics Files: Progressive Lenses. Paris: Varilux University, 2006.*
Bara, S., et al., "Wide-Field Compensation of Monochromatic Eye Aberrations: Expected Performance and Design Trade-Offs," *Optical Society of America*, Jan. 2003, pp. 1-10, vol. 20, No. 1.
Soloway, B., "Wavefront measurement methods discussed: Zernike polynomial's role as optimal methodology for describing wavefront error recently challenged. (Zernike versus Fourier)," *Ophthalmology Times*, Sep. 15, 2004, pp. 58-59, vol. 29, Issue 18.
International Search Report for PCT/US2008/087035, mailed Apr. 24, 2009, 2 pages.
Royce, "A Better Method of Measuring Optical Performance: Move over P-V and make way for Strehl," Precision Optical Performance, downloaded from rfroyce.com on Jan. 23, 2008.

* cited by examiner

*Primary Examiner*—Scott J Sugarman
*Assistant Examiner*—Zachary Wilkes
(74) *Attorney, Agent, or Firm*—Morrison & Foerster LLP (57) ABSTRACT

Embodiments of the invention pertain to a method for producing a spectacle lens with optimal correction across the entire lens taking into account the patient's complete measured wavefront. Specific embodiments can also take into account one or more additional factors such as vertex distance, SEG height, pantoscopic tilt, and use conditions. The lens wavefront can be achieved by optimizing a corrected wavefront, where the corrected wavefront is the combined effect of the patient's measured wavefront and the lens wavefront. The optimization of the corrected wavefront can involve representing the measured wavefront and the lens wavefront on a grid. In an embodiment, the grid can lie in a plane. During the optimization, a subset of the grid can be used for the representation of the measured wavefront at a point on the grid so as to take into account the portions of the measured wavefront that contribute to the corrected wavefront at that point on the grid.

7 Claims, 11 Drawing Sheets

Lens Profile Development Processing Steps

FIG. 1 Lens Profile Development Processing Steps

CUSTOMIZED Z-LENS DESIGN PROGRAM

BACKGROUND OF INVENTION

Ocular lenses are worn by many people to correct vision problems. Vision problems are caused by aberrations of the light rays entering the eyes. These include low order aberrations, such as myopia, hyperopia, and astigmatism, and higher order aberrations, such as spherical, coma, trefoil, and chromatic aberrations. Because the distortion introduced by aberrations into an optical system significantly degrades the quality of the images on the image plane of such system, there are advantages to the reduction of those aberrations.

Ocular lenses are typically made by writing prescriptions to lens blanks. This is accomplished by altering the topography of the surface of a lens blank.

Recently, attention has been given to methods of writing a low order lens using a patient's measured wavefront information. Currently, several techniques can be utilized to determine the optimum low order refraction from the high order, including: the Gaussian Least Squares Fit, point spread optimization, and neural network analysis. Some of these techniques may be employed to not only derive the best low order prescription from the high order values, but may also be used to "fit" an optimum wavefront across an entire spectacle lens based on the patient's measured wavefront.

Using one or more of these fitting techniques may yield a better refraction than conventional subjective refractions in the center zone, but consideration must be given to off-axis gaze angles. In particular, one considerable disadvantage of traditional lens manufacturing is that that many people experience distortion when looking off-center outside the central region, commonly called "swim".

Accordingly, there is a need for a method of determining a wavefront for a patient's spectacle based on the patient's measured wavefront, in such a way to reduce distortion when the patient looks off center outside the central region.

BRIEF SUMMARY

The subject invention provides methods for determining a wavefront for a lens from a patient's measured wavefront. The wavefront can be used for producing a spectacle lens with optimal correction across the entire lens taking into account the patient's complete measured wavefront. Specific embodiments can also take into account one or more additional factors such as vertex distance, SEG height, pantoscopic tilt, and use conditions.

The lens wavefront can be achieved by optimizing a corrected wavefront, where the corrected wavefront is the combined effect of the patient's measured wavefront and the lens wavefront. In one embodiment of the subject invention, the optimization of the corrected wavefront involves representing the measured wavefront and the lens wavefront on a grid. In an embodiment, the grid can lie in a plane. During the optimization, a subset of the grid can be used for the representation of the measured wavefront at a point on the grid so as to take into account the portions of the measured wavefront that contribute to the corrected wavefront at that point on the grid.

BRIEF DESCRIPTION OF FIGURES

FIGS. 11A-1D show an example of coma.

DETAILED DISCLOSURE

The subject invention provides methods for determining a wavefront for a lens from a patient's measured wavefront. The wavefront can be used for producing a spectacle lens with optimal correction across the entire lens taking into account the patient's complete measured wavefront. Specific embodiments can also take into account one or more additional factors such as vertex distance, SEG height, pantoscopic tilt, and use conditions.

The lens wavefront can be achieved by optimizing a corrected wavefront, where the corrected wavefront is the combined effect of the patient's measured wavefront and the lens wavefront. The optimization of the corrected wavefront can involve representing the measured wavefront and the lens wavefront on a grid. In one embodiment, the grid can lie in a plane. During the optimization, a subset of the grid can be used for the representation of the measured wavefront at a point on the grid so as to take into account the portions of the measured wavefront that contribute to the corrected wavefront at that point on the grid.

One embodiment of the invention utilizes the hill climbing optimization technique used in the Gaussian Least Squares Fit and point spread optimization software to fit an optimal wavefront across a specified surface larger than that of the measured wavefront. The desired wavefront is projected from a number of points emanating in multiple directions from a nominal axis of rotation representing the center of the eye. The wavefront pattern used can be solely based upon the low order, or can also include some or all the high order as well.

Each position of the wavefront as projected from the center of the eye can be convolved with a weighting function across the lens to enhance or emphasize the wavefront in certain areas while allowing other areas to be de-emphasized. The wavefront is best fit along a surface representing a paraxial lens representing the neutral axis of a lens. This paraxial lens is fixed in space at a specified central vertex distance and follows the basic lens design curvature of the chosen blank lens. The basic lens design curvature may be simply derived from the central lower-order prescription or may be used in conjunction with the high order and other factors such as vertex distance.

Figure 1:
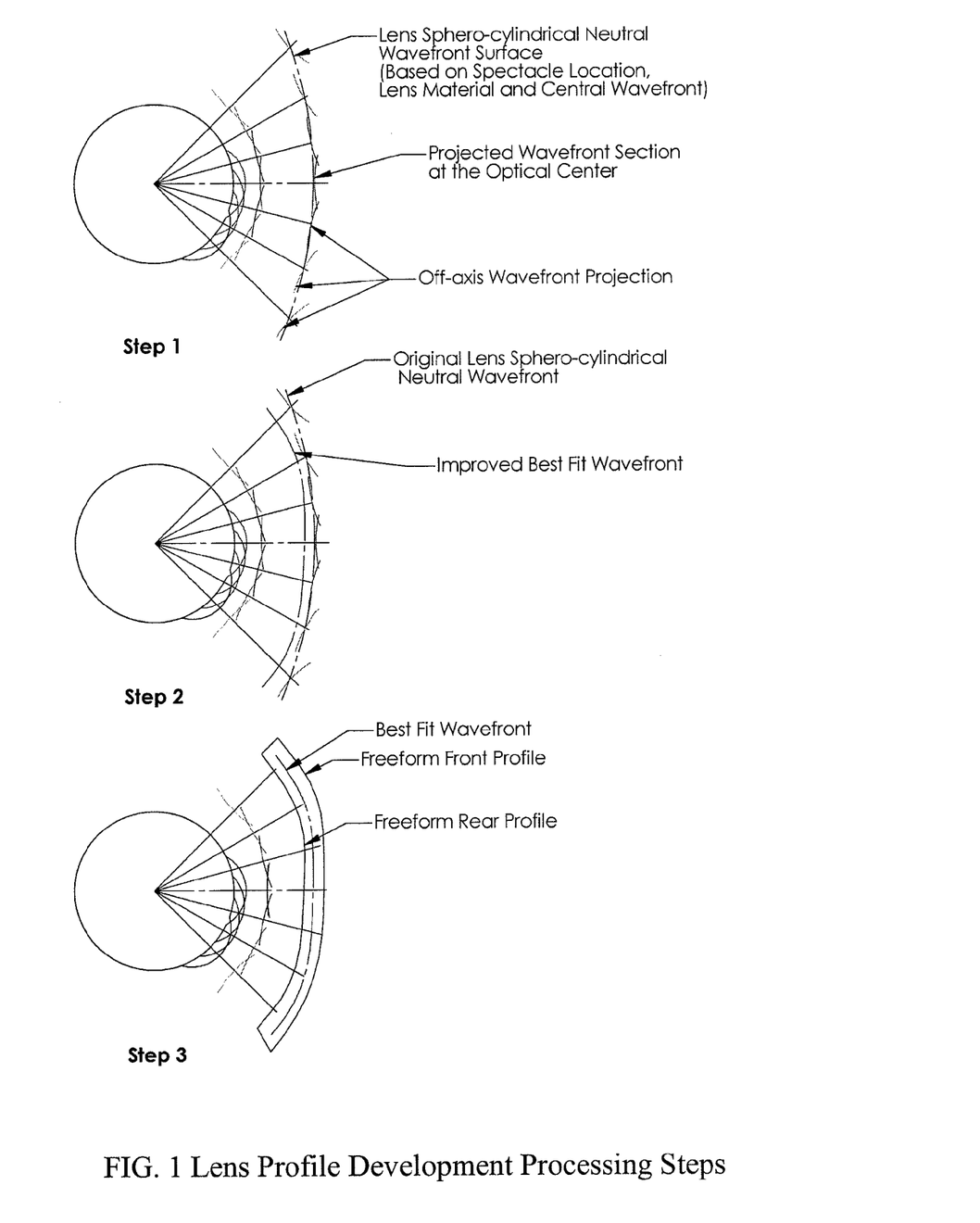
FIG. 1 shows the steps for a method for producing a spectacle lens in accordance with an embodiment of the subject invention.
Figure 2:
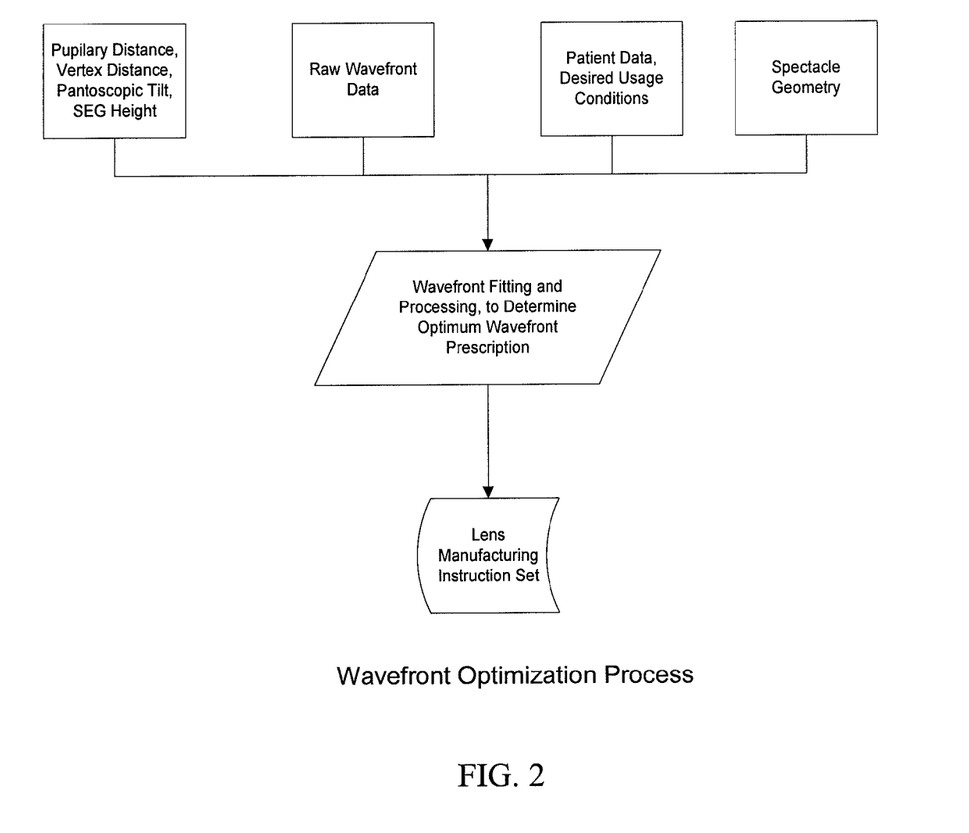
FIG. 2 shows a flow chart in accordance with an embodiment of the subject invention.

The final wavefront can be fitted with one or more of the following inputs:
Wavefront
Papillary Distance Vertex Distance
Pantoscopic Tilt
SEG Height
Pupil Diameter
Conditions under which the lens will be used (day, office, night, etc)
Age
OD Subjective refraction
ADD Value
Spectacle Geometry FIG. 1 shows the steps for one embodiment of a method for producing a spectacle lens in accordance with the subject invention and FIG. 2 shows a flowchart indicating the flow of information in accordance with an embodiment of a wavefront optimization method. In one embodiment, vertex distance and its effect on the lens power and astigmatism can be compensated for in the wavefront fitting process. The output of the wavefront fitting software process (steps 1 & 2 in FIG. 1) is a set of instructions that facilitates production of a custom lens.

Various techniques may be utilized to generate the actual lens. For example; the instructions may include a surface map for front and/or back surfaces of a lens, or a points file that can be fed into a freeform lens generator, to cut custom front and back surfaces. Other approaches may utilize a changeable refractive index layer within the lens blank that can be customized with the information from the fitting software. Yet another approach can use an inkjet deposition of different refractive indices across a lens surface to generate a corrected wavefront based on the fitting software output. In yet another approach, stereo lithography may be used in conjunction with casting, or combination of any of the above techniques can be combined to achieve the custom lens manufacturing.

Step 3 in FIG. 1 represents a freeform grinding approach to lens manufacturing. Casting, inkjet, and sandwiched changeable refractive index approaches as known in the art, can also be utilized.

If utilizing the freeform grinding approach the final step in the wavefront fitting software can generate shape of the front and back surface of the lens to achieve the given wavefront. Development of the shape of the front and back surface can also take into account the distortions from lens thickness variations to minimize distortions. The output of the fitted wavefront software can, in an embodiment, be a points file, which can subsequently be transferred into a freeform lens generator for manufacturing the lens. The resulting lens can be essentially optimized across the entire lens and customized for each patient based on all the input parameters. This freeform grinding technique can be utilized in conjunction with the refractive index changing material to further tune or enhance the refractive properties after lens grinding and polishing.

In one embodiment, a grid of shifts (rather than rotations) for measured and target pupil wavefronts is used, represented mathematically by images. The target wavefront can be used as the lens wavefront. From the measured wavefront, the target wavefront can be determined via one or more embodiments of the invention. A variety of configurations can be used to implement the target wavefront via an eyeglass for the patient.

As an example, a single lens with two surfaces can be used to create an eyeglass for a patient, where one or both of the lens surfaces can be controlled to effect the wavefront for the lens. Alternatively, two lens blanks each having two surfaces can be used with a variable index polymeric material between the two lens blanks, where one or more of the four lens blank surfaces and/or the polymeric material can be controlled to effect the wavefront for the lens. The lens surface(s) and/or variable cured index of the polymeric material of the polymeric material are described in a two-dimensional plane corresponding to the height of the surface(s) or the projection of the index layer(s) onto a plane.

Figure 3:
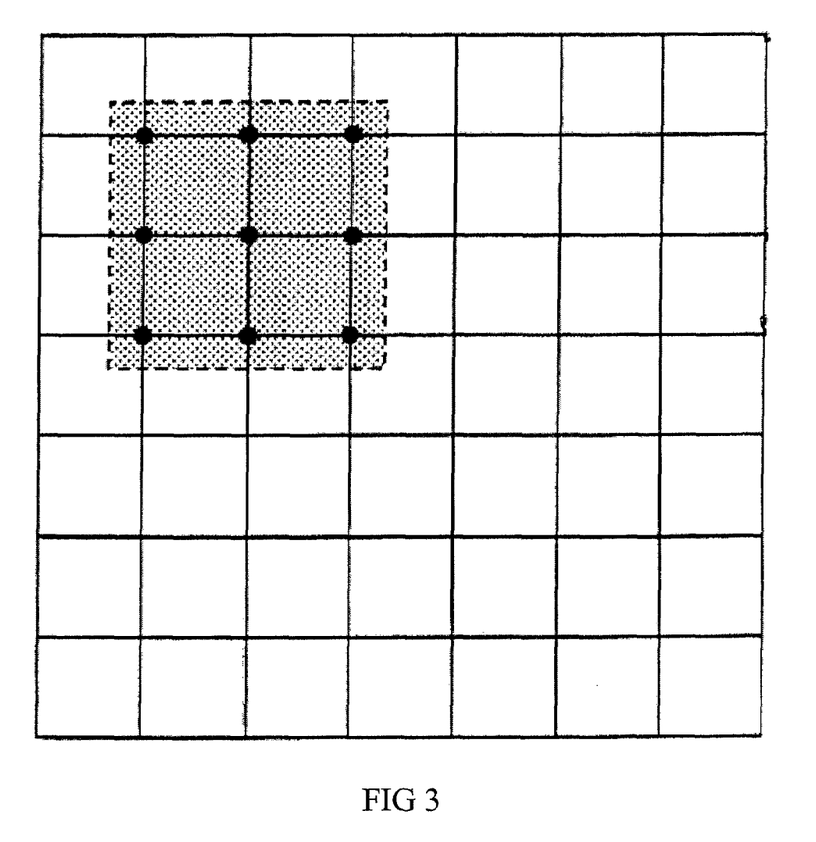
FIG. 3 shows a top view of spectacle and pupil samples as images at particular shift (gaze).
Figure 4:
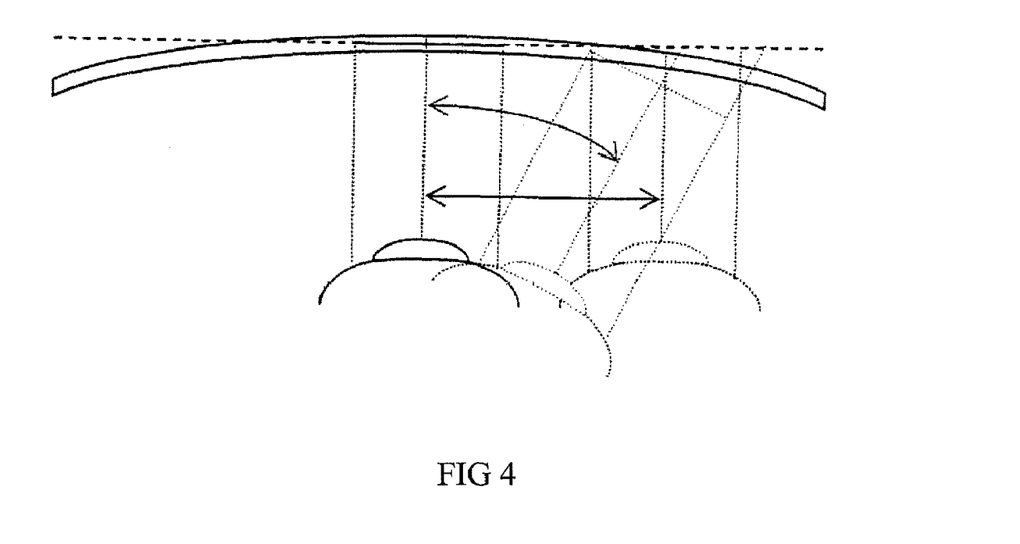
FIG. 4 shows a side view of spectacle and eye, on the left with corresponding dotted lines, with gaze rotation shown by the curved arrow and the rotated eye and corresponding dotted lines the curved arrow is pointing to and gaze shift shown by the straight arrow and the shifted eye and corresponding dotted lines the straight arrow is pointing to on the right.
Figure 5:
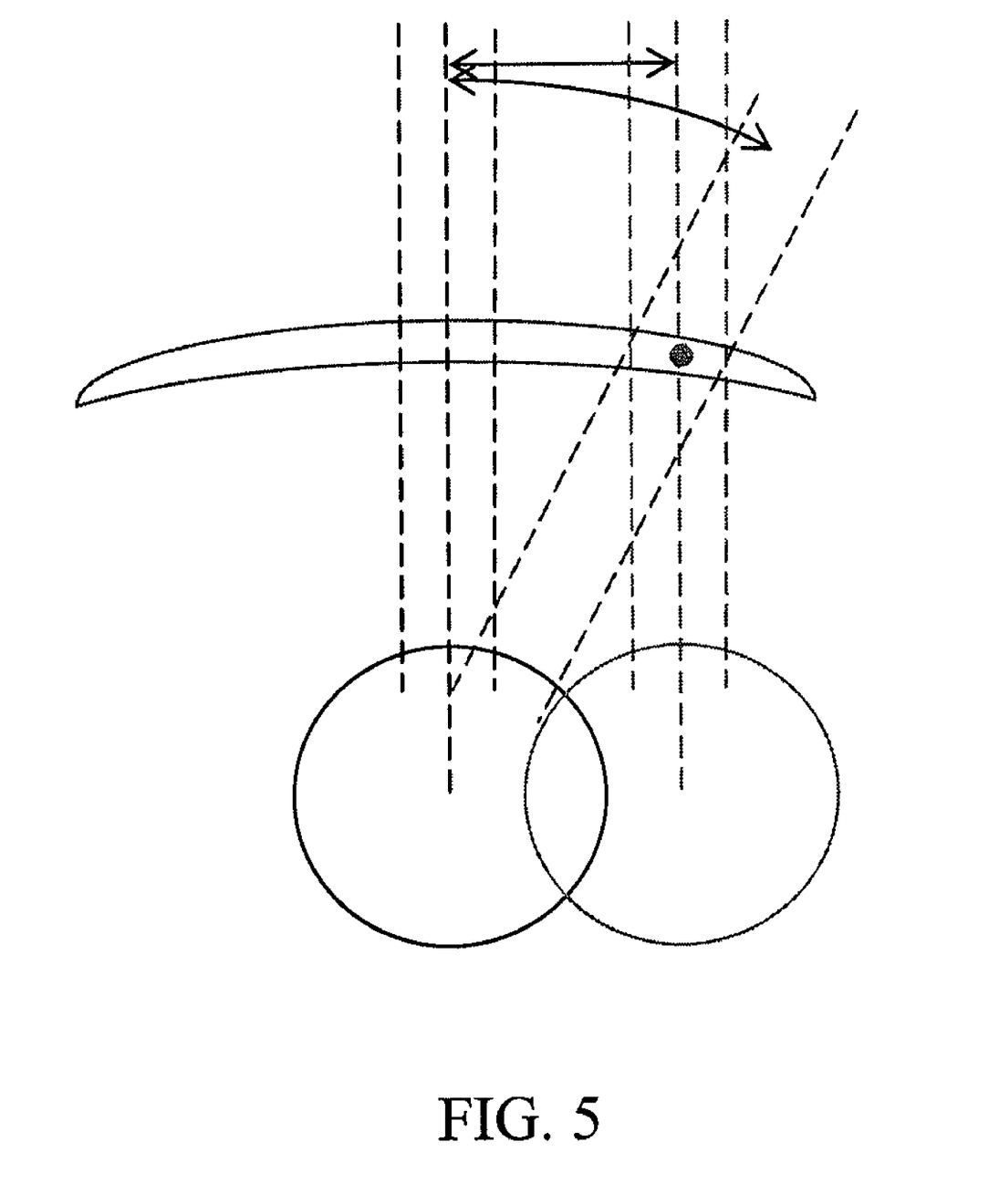
FIG. 5 shows a schematic representation of an approximation of representing the i-th direction as the i-th shift.
Figure 6:
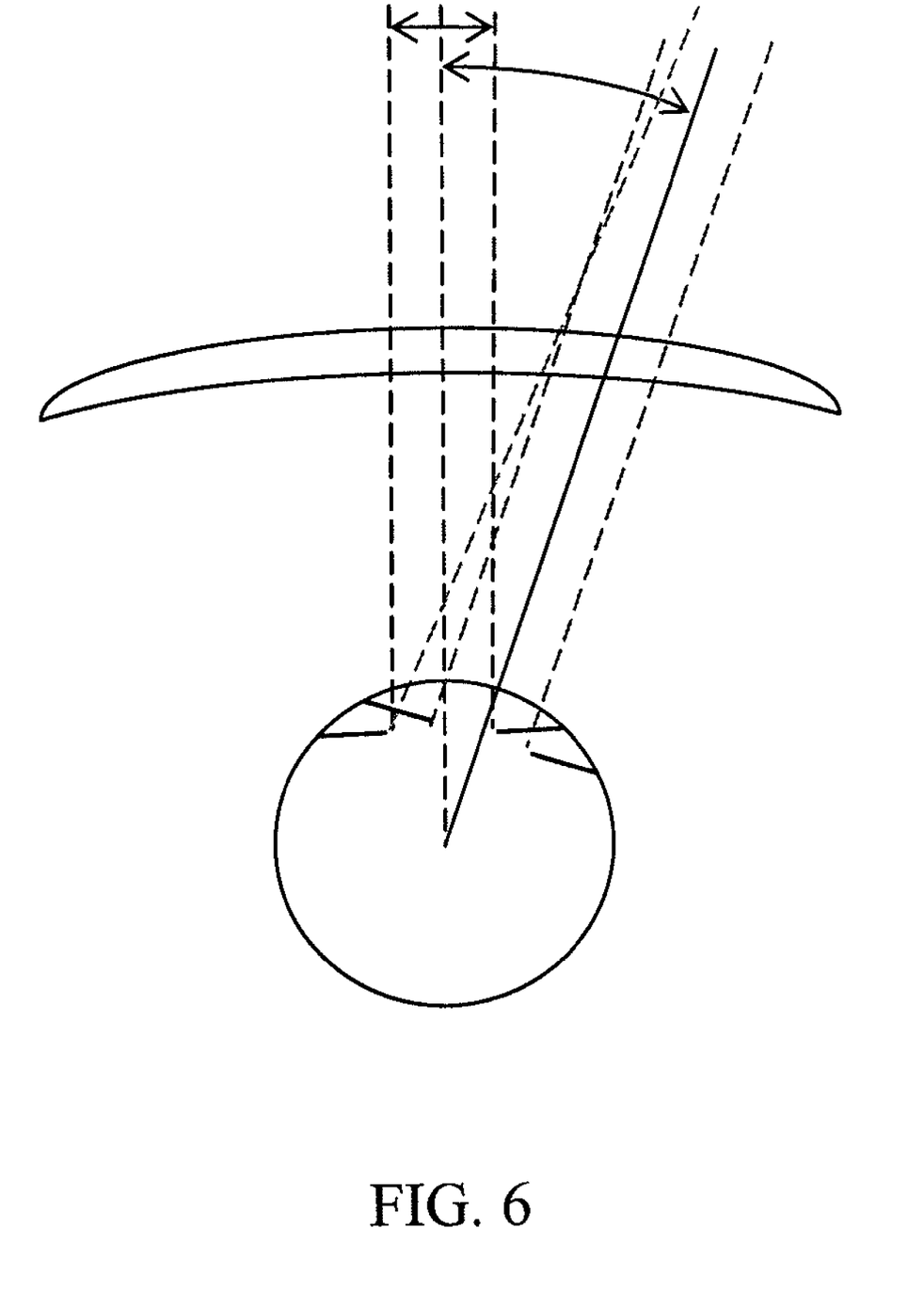
FIG. 6 shows a comparison of off-axis versus transverse correction for spectacle lens applications.
Figure 7:
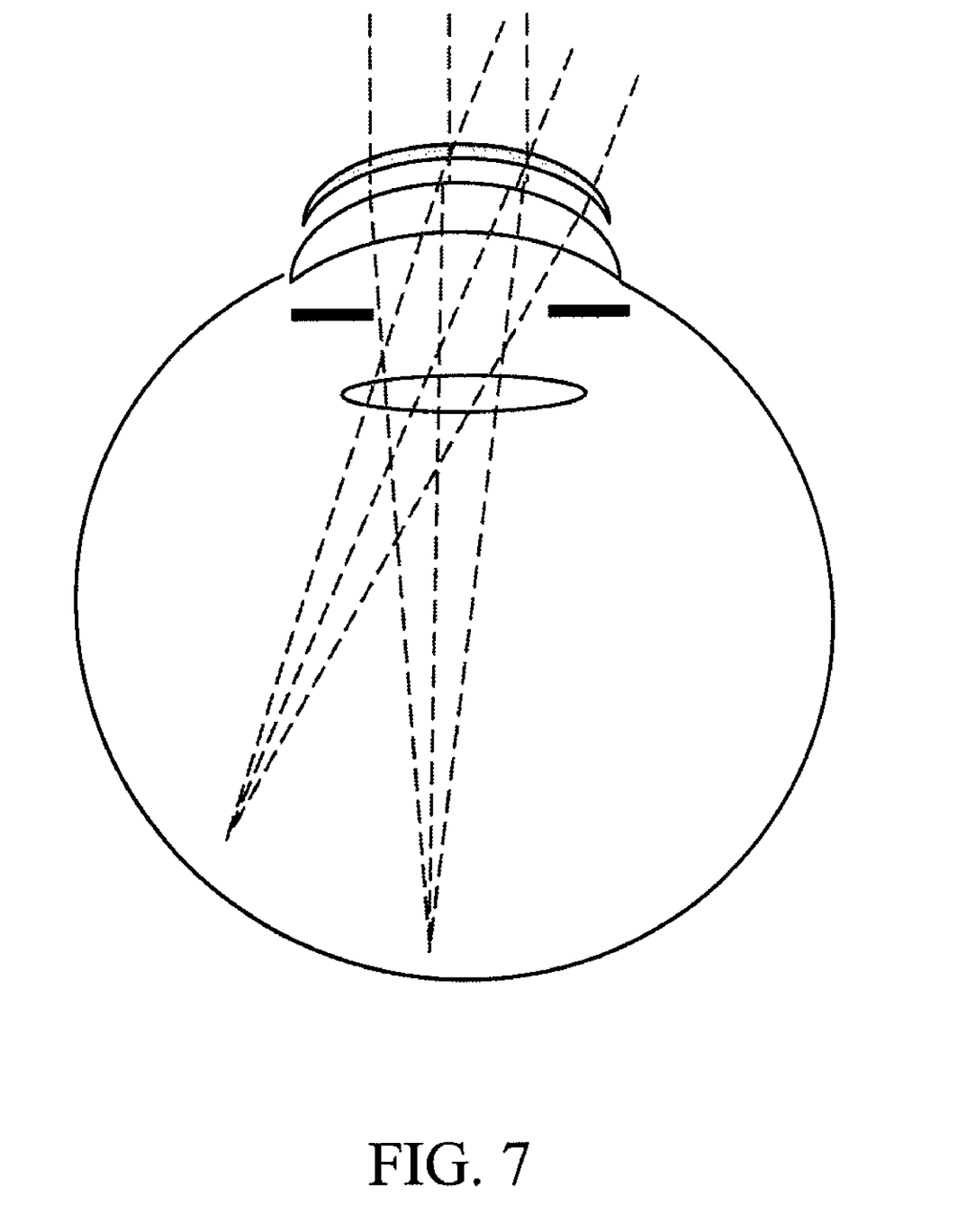
FIG. 7 shows a schematic representation of a transverse correction for a contact lens application.
Figure 8:
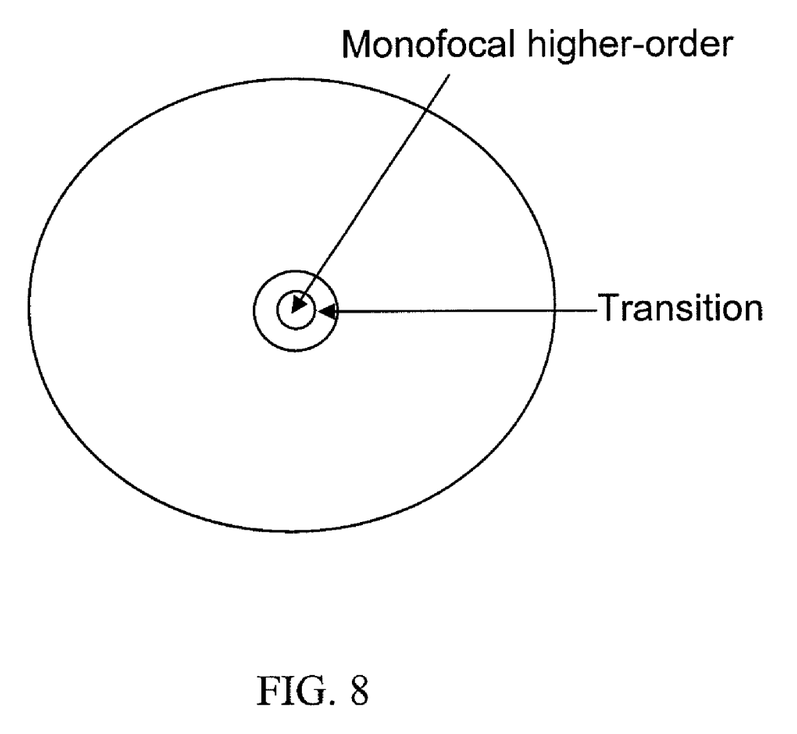
FIG. 8 shows a schematic representation of a lens blank with a monofocal higher-order region and a transition zone.

Aberrations are measured as components in an orthogonal expansion of the pupil sampled on the same grid spacing. In a specific embodiment, the grid spacing is about 0.5 mm and in another embodiment the grid spacing is about 0.1 mm. In an embodiment using Zernike polynomials, the components can be made orthogonal for the chosen pupil size due to discrete sampling. As an example, the components can be made orthogonal through a process such as Gram-Schmidt orthogonalization. Orthogonal components of aberrations for pupils centered at a specific point on the spectacle may then be computed by sample-by-sample multiplication (inner product) of the aberration component image with the lens (height or projection) image centered at the point of interest, as in FIG. 3. FIG. 3 shows a top view of spectacle and pupil samples as images at particular shift (gaze), which can be used for computation of aberrations for pupils having a diameter of 3 samples, centered at a chosen coordinate on a spectacle grid having a diameter of 8 samples.

Zernike polynomials are orthogonal and when samples are taken, approximations of Zernike polynomials can be created. In one embodiment, the approximations of Zernike polynomials can then be modified to make orthogonal polynomials, so as to create new polynomials.

In an embodiment, points on the pupil outside the pupil diameter are assumed zero. Non-squared pupil shapes may be formed by zeroing select points within the square of pupil diameter. Mathematically, the process of computing the inner product centered at all possible locations on the grid is a cross correlation, which may be implemented with a fast convolution algorithm. An image can be produced for each Zernike via the cross-correlation. The image for each Zernike can be used to create a target and an error. The error can be used to produce an error discrimination, or a weighted sum of all pixels in the image square.

In a specific embodiment, a grid size and spacing is chosen to represent the lens and pupil in a plane. An example of such a grid is shown in FIG. 3. The aberrations of interest are orthogonalized on the grid at the chosen pupil size. Then a given aberration centered at every point may be estimated by cross-correlation of the orthogonalized Zernike image and the spectacle image, resulting in an image for each Zernike component. An error image for each point on the lens may be estimated as a difference between the computed and desired Zernike aberration centered at each point in the image.

The desired correction is, to a first approximation, assumed to be constant in this plane with a shift corresponding to a given gaze angle. The rotation is otherwise neglected as shown in FIG. 2. For large gaze angles, the effect of rotation can be compensated by providing a spatially-varying correction target. The spatially-varying target can be approximated by rotating the paraxial target.

Simple convolution may be replaced with a more exact geometric calculation of the ray-surface intersection corresponding to a ray-tracing-style algorithm over a fixed grid. Other grid geometries may be used (e.g., hexagonal instead of rectangular). The result is essentially a spatially varying sample spacing and convolution, increasing computation time.

Other metrics of surface error may be computed from the Zernike component error images, as done with single pupil representations. Images of sphere/cylinder/values (or errors from desired) may be computed by applying the usual conversion on a pixel-by-pixel basis for example.

Total root-mean-square (rms) may be represented by either the sum of all component terms squared for a particular pupil location, or the sum of all pixels squared (and properly normalized) within the pupil. This may be achieved by cross-correlations of a pupil-sized aperture of ones with an image of the lens values squared. Total high order may be computed by subtracting the low order aberration images from the total rms image. High order error may be computed by also subtracting the target high order images, squared pixel-by-pixel. For certain error choices optimizing error this may be mathematically equivalent to known regularization algorithms.

A total error discriminant may be generated by summing desired error images over the entire lens. A pixel-by-pixel weighting may be incorporated to selectively weight the error at various regions in the lens, and this may be done independently for each Zernike component. Standard optimization procedures (e.g., convex programming) may be used to produce a lens image that minimizes the error discriminant. If the lens image is sufficiently small, the cross-correlation may be represented as a matrix multiplication further simplifying the application of optimization algorithms known in the art. For larger image sizes this may be impractical, but may still be used to adapt the algorithm to the problem before implementing with fast convolution algorithms.

Constraints on the error may also be used in the optimization that would be represented by constraint images of max and/or min Zernike components or functions thereof. An example of a constraint that can be utilized is that the error for a certain Zernike cannot be above a certain threshold for a certain area.

Free-floating points, such as boundaries, may be handled by setting weights to zero or very small for those points. This allows the optimized region to be smaller than the actual grid, the optimized region to have an arbitrary shape, and/or the optimized region to only be optimized for points that will ultimately be used. In a specific embodiment, the patient-selected frame outline may be input as the region of optimization. As there can be an infinite number of solutions, an attempt can be made to optimize a certain shape inside of the lenses, such as the spectacle shape. An example of a certain shape that can be optimized is to optimize within the shape of the frame that the lens will be used by, for example, using a zero weight outside of the frame.

Fixed points, which are given prior to optimization and remain unchanged, may be provided by using the points to compute correction but not applying it to them in the optimization algorithm. This can be used for boundaries, so as to only optimize for certain portions of lenses.

Grid(s) of constraints may be converted into a weighting and/or target (for unconstrained optimization) via a separate optimization procedure.

Multiple surfaces may be optimized simultaneously. As an example, two grids can be optimized simultaneously or each grid point can have two numbers associated with it to be optimized.

The patient's prescription (including high order) may be used as target, including deterministic variations with gaze if available.

Example 1

Simple Alignment Tolerant Lens

For purposes of this example, lower case bold letters denote matrices (or equivalently, images), which describe either the two-dimensional (single-surface) lens as a optical-path delay (OPD) map, or a two-dimensional wavefront, also as an OPD map.

$a_{i,j}$ Corrected wavefront aberration in the $(i,j)^{th}$ position.

i, j Indices $i^{th}$ horizontal and $i^{th}$ vertical positions.

n, m Indices of matrix elements.

L Total number of pixels on side of (square) pupil and aberration matrices.

N Total number of pixels on side of (square) spectacle OPD matrix.

p, Pupil aberration OPD, $p_{i,j}$ pupil aberration in the $(i,j)^{th}$ position if it changes with gaze.

s Spectacle OPD over entire range of lens, e.g. 50 mm diameter g Matrix describing weighting of error over pupil $z_k$ k-th (sampled) Zernike wavefront matrix w(i,j), Weighting over angle, $w_k(i,j)$ Weighting over angle for the $k^{th}$ Zernike term f Objective function An assumption can be made that an optimization of image quality for a lens over a range of gaze angles can be well approximated by an optimization of image quality over a range of translations. The rotation of the eye relative to the lens is, therefore, ignored in this example. The desired OPD calculated through optimization can be converted to, for example, a surface or pair of surfaces via a ray-tracing application.

The corrected wavefront aberration in the $(i,j)^{th}$ position, including both the pupil aberration p and the corresponding apertured portion of the spectacle s, is described as $$a_{i,j}(n,m) = p(n,m) + s(n+i, m+j); \quad n,m = -\frac{L}{2}, \ldots, \frac{L}{2} \quad (1)$$

a, p, and s are matrices. The total error to be optimized will be a function of all the $a_{i,j}$. The matrices can have zeroes as entries for input data or output data that is, for example, circular, rectangular, or has a non-square pattern. The simplest function is the total squared error over all shifts with weightings over both the shifts and the pupil, which can be represented as shown in Equation (2).

$$f = \sum_{i,j} w(i,j) \sum_{n,m} g(n,m) [a_{i,j}(n,m)]^2 \quad (2)$$

One approach to optimize the corrected wavefront is to preferentially select certain Zernike terms to be corrected or excluded. An example of preferential selection of certain Zernike terms is to only correct astigmatism for a Progressive-Addition Lens (PAL) design. To select the component of the chosen Zernike term(s) from the full wavefront aberration we make use of the orthonomality of Zernikes and simply take the inner product of each Zernike with the wavefront in Equation (1).

$$a_{i,j}(n, m) = z_0 \sum_{n,m} \{z_0(n, m)a_{i,j}(n, m)\} + \tag{3}$$

$$z_1 \sum_{n,m} \{z_1(n, m)a_{i,j}(n, m)\} + \ldots$$

$$= \sum_{k=0}^{\infty} z_k c_k(i, j)$$

The coefficient matrix for the k-th Zernike, $c_k(i, j)$, can be computed as $$c_k(i, j) = \sum_{n,m} \{z_k(n, m)a_{i,j}(n, m)\} \tag{4}$$

$$= z_k * a_{i,j}$$

which uses the cross-correlation operation or, equivalently, the convolution operation implemented appropriately.

Particular Zernike components of the aberration can be selectively weighted by weighting the component in (3)

$$a'_{i,j}(n, m) = \sum_{k=0}^{\infty} w_k(i, j)c_k(i, j)z_k \tag{5}$$

The appropriate $w_k$ may be set to zero to ignore certain components.

The simplest approach, and one of very few that can be solved analytically, is to optimize a weighted total squared error over all gaze positions, or shifts, where the error is defined according some carefully chosen and/or excluded combination of Zernikes.

It is apparent that the minimum least-squares optimum over an angle-range larger than the pupil diameter with no weighting will result in a purely low-order solution. However if a weighting is used it is possible to trade off improvement in some areas for others.

Combining equations (2) and (5), the squared error objective is then $$f = \sum_{i,j} \sum_{n,m} g(n, m) \left[ \sum_{k=0}^{\infty} w_k(i, j)c_k(i, j)z_k \right]^2 \tag{6}$$

$$= \sum_{i,j} \sum_{n,m} g(n, m) \left[ \sum_{k=0}^{\infty} w_k(i, j)(z_k * (p(n, m) + s(n + i, m + j)))z_k \right]^2$$

which may be solved via standard optimization algorithms for the optimal s.

Making the weighting w (n,m) the same for every Zernike term allows an analytical solution. Setting the gradient of equation (6) with respect to s equal to zero yields an optimized result which can be written as follows:

$$s = -\{w*(g \times p)\}/\{w*g\} \tag{7}$$

The "×" and "/" operators indicate element-by-element multiplication or division respectively, and the "*" operator indicates two-dimensional convolution.

Using a uniform pupil-weighting further simplifies equation (7) to $$s = -\{w*p\}/\{w*1\} \tag{8}$$

Where 1 is simply a matrix of ones, resulting in a low-pass filtered w in the denominator term. So the result is a convolution of the weighting with the aberration that is normalized by a filtered version of the weighting.

Some simulated examples for certain zernike terms are provided in FIGS. 10A-10D, FIGS. 11A-11D, and FIGS. 12A-12D, where FIGS. 10A-10D show an example of trefoil, FIGS. 11A-11D show an example of coma, and FIGS. 12A-12D show an example of spherical aberration. Note that the amplitudes are normalized for a 1 um rms aberration, and the y-axis is normalized to the zernike diameter. One-dimensional cross-sections of the lens, error are provided. Again, FIGS. 10A-10D show the results for trefoil; FIGS. 11A-11D show the results for coma; and FIGS. 12A-12D show the results for spherical aberration.

Referring to Example 1, several different methods can be reflected in different choices of g, the matrix describing weighting or error over pupil, with $q_{ij}$ being effective pupil aberration for the i, j position and h being a matrix describing weighting of wavefront over pupil. Examples of several methods are provided in Table 1.

TABLE 1

| Mathematical Step | Description of Method |
|---|---|
| g = I, the identity matrix | Standard Least Squares |
| $g_w$ = diag{g}, diagonal matrix | Least Squares weighted over pupil |
| g = $hg_w$h, h = $z_3z_3^T + z_5z_5^T$ | Minimum Astigmatism - PAL design |
| g = $hg_w$h, h = I − $z_0z_0^T$ | Free Varying Piston |
| g = $hg_w$h, h = I − $z_0z_0^T − z_1z_1^T − z_2z_2^T$ | Free Varying Tilt - distortion allowed |
| $q_{ij} = p_{ij} − i\, c_1z_1 − i\, c_2(i)z_2$ | Constantly Changing Tilt - Magnification |

Another approach can require an "unknown prescribed Zernike". This can be used, for example, to yield a tilt that is constant (as possible) over the lens but not necessarily zero. For certain aberrations this can result in an improved vision quality by allowing some magnification, which in this treatment can be referred to as linear distortion. This can be achieved by iteratively varying the values for $c_{1,desired}$ and $c_{2,desired}$ with some allowable range and choosing the pair that results in the lowest error minimum.

Aberration Bandwidth

An approach at optimizing a metric based on the point-spread function (PSF) can be performed via consideration of the spatial "bandwidth" as a metric of the PSF at a specific gaze angle. If a wavefront can be described as a two-dimensional single-component FM signal, then its local spatial frequency content at a given point can be estimated form the spatial derivatives of the phase. By estimating the average mean squared value of the spatial derivative of the wavefront, an estimate of the bandwidth of the PSF can be produced.

An estimate for the averaged bandwidth of the PSF can be described as Da, where D is a matrix that computes the averaged local derivative via finite differences. There is a variety of possible choices for D to approximate a derivative.

An approach similar to the use of a matrix that computes the averaged local derivative via finite differences approach of Example 1, but using derivatives of the pupil and spectacle, can be used.

In another embodiment, D can be selected to approximate a second derivative, in order to approximate power matching.

Region-Based Optimization

In an embodiment, optimization can be performed using a standard iterative approach such as Gradient Descent with some chosen boundary conditions. These boundary conditions can describe the required outcome at the edges of the lens as well as in zones in its interior. A variety of different applications can be addressed by selecting these regions.

Transition Zones

Transition zone based lens designs have the requirement of perfection for the axial ray and for the correction at some outer radius to be a constant (or low-order). Therefore, the single zone's correction can be predetermined as some high-order correction, then the optimization can vary only a narrow region outside this zone to find the optimum lens. The remaining region outside this transition zone can be required to be some flat or low-order correction.

Progressive-Addition Lenses

Progressive-Addition Lenses (PAL's) have required low-order correction in a pair of zones, with some varying power along a line connecting them. Typically, the rest of the lens is then optimized to reduce distortion. In an embodiment of the subject invention, the lens can be optimized to similarly reduce distortion. The lens can be optimized to reduced distortion via, for example, power matching, matching second order wavefronts only, or full-wavefront matching with a varying tilt.

Example 2

Simple Rotation and Alignment Tolerant Lens Design

This Example uses a method for optimizing the correction "programmed" onto a higher-order contact lens. Contact lenses can be designed to be in a certain orientation, but can still rotate with respect to this orientation and can slide as well so as to become decentralized. The unpredictable rotation and decentration of the lens during normal wearing can be addressed. Given a range of rotations and decentrations, the contact lens design is optimized to improve vision throughout the entire range by minimizing the total wavefront error summed over the ranges. The optimum over decentrations may be computed as in Equation (7) provided in Example 1. The optimum over rotations is computed as follows.

The error discriminant is:

$$f = \sum_\theta w(\theta) \sum_{n,m} [p(n,m) + s(n\cos\theta + m\sin\theta, -n\sin\theta + m\cos\theta)]^2 \quad (9)$$

The optimal result is similar conceptually to the decentration case.

$$s = -\frac{1}{\sum_\theta w(\theta)} \left\{ \sum_\theta w(\theta) p(n\cos\theta - m\sin\theta, n\sin\theta + m\cos\theta) \right\} \quad (10)$$

Figure 9:
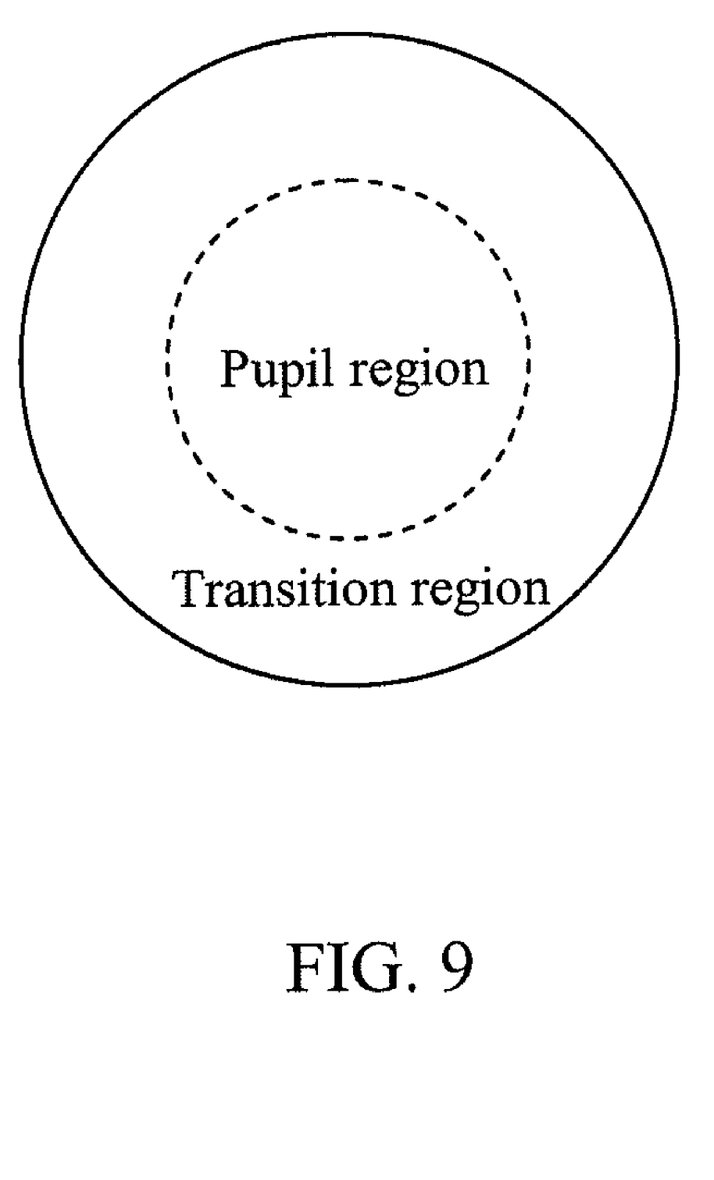
FIG. 9 shows a lens image.
Figure 10A:
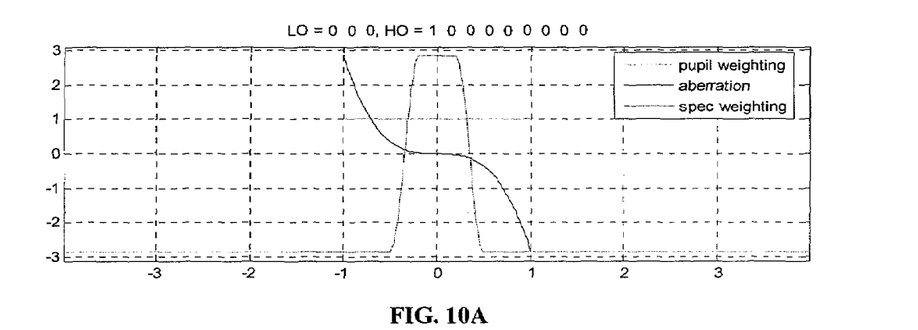
FIGS. 10A-10D show an example of trefoil.
Figure 10B:
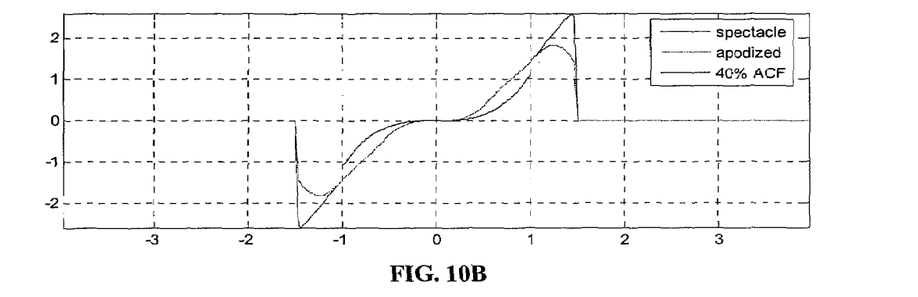
Figure 10C:
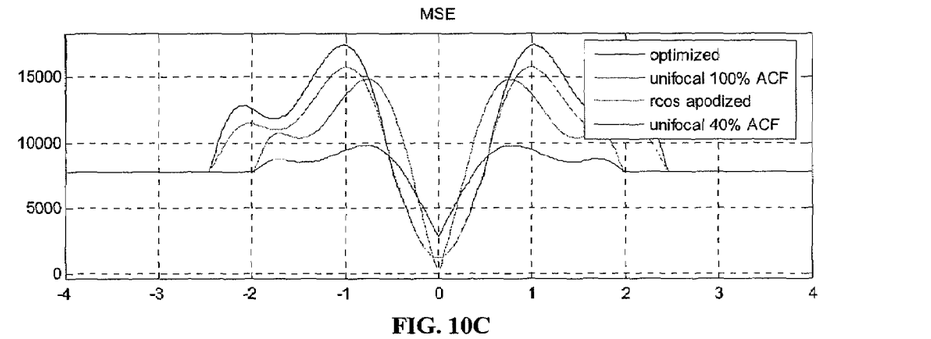
Figure 10D:
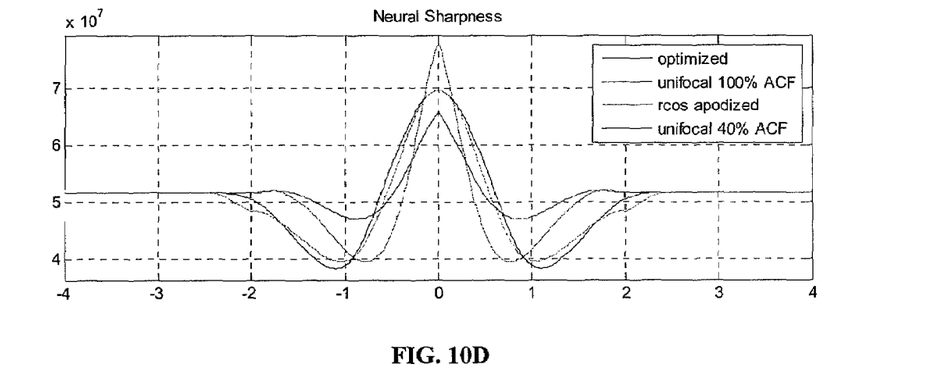
Figure 11A:
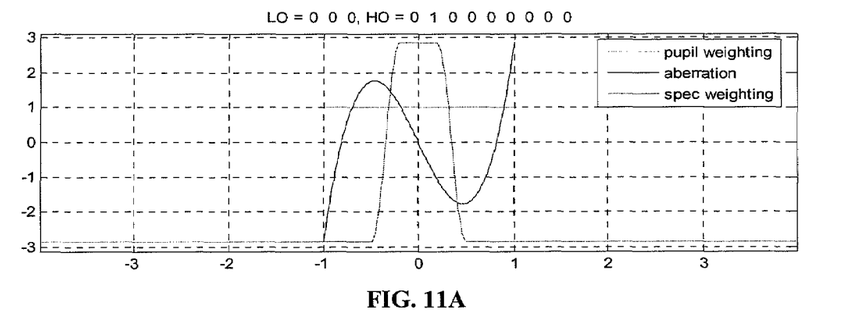
Figure 11B:
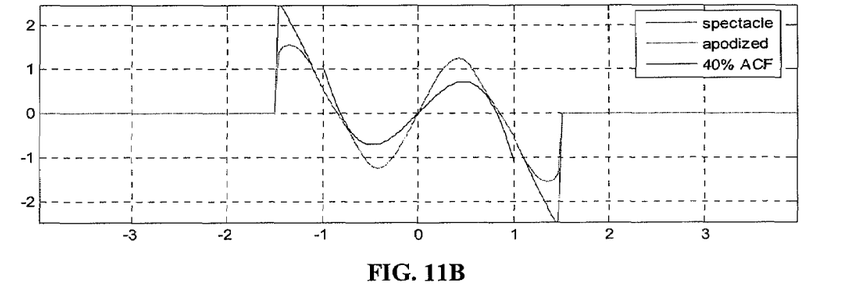
Figure 11C:
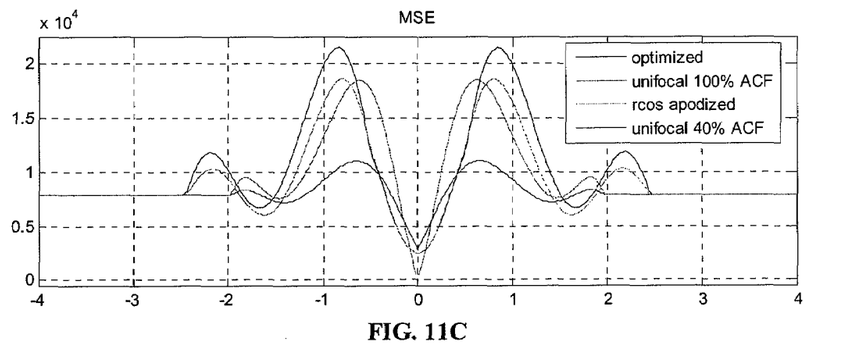
Figure 11D:
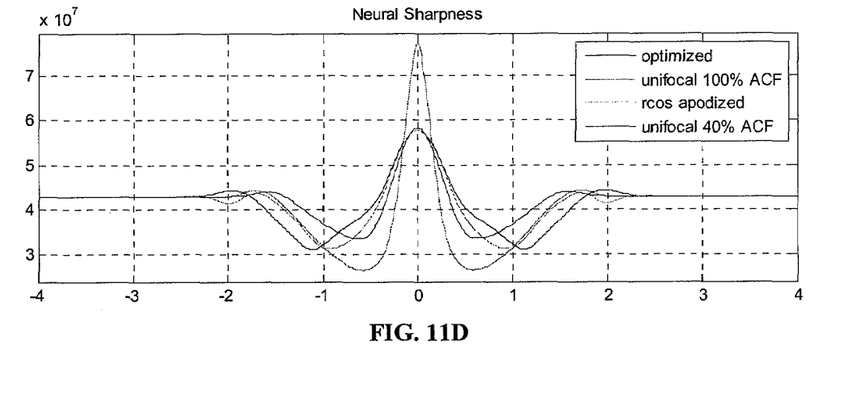
Figure 12A:
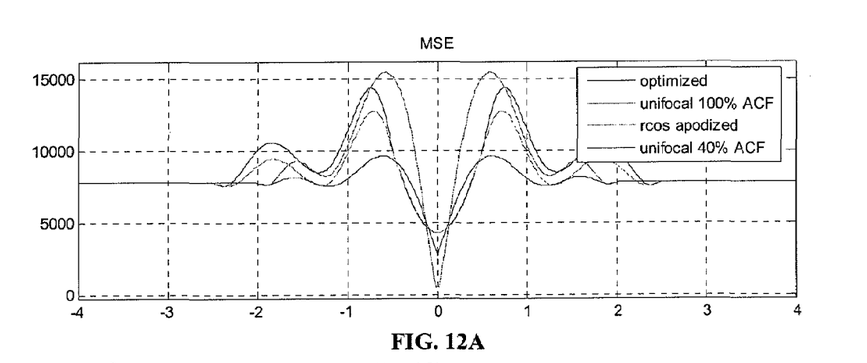
FIGS. 12A-12D show an example of spherical aberration.
Figure 12B:
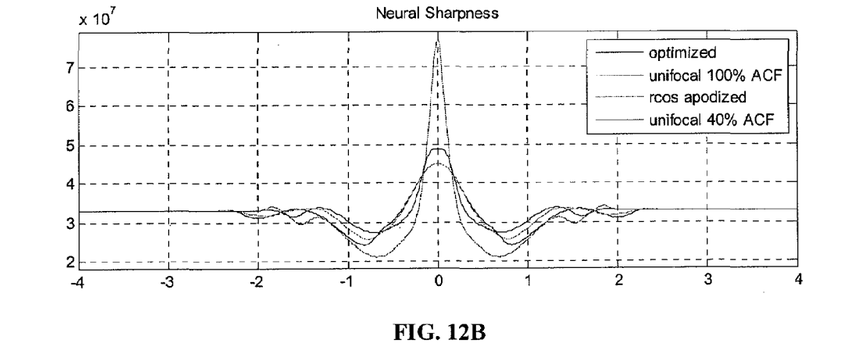
Figure 12C:
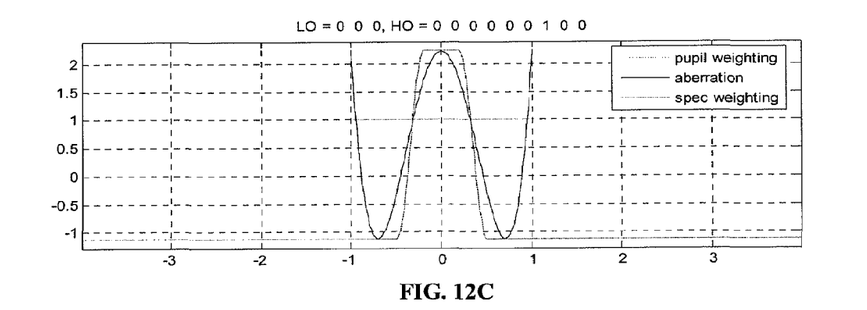
Figure 12D:
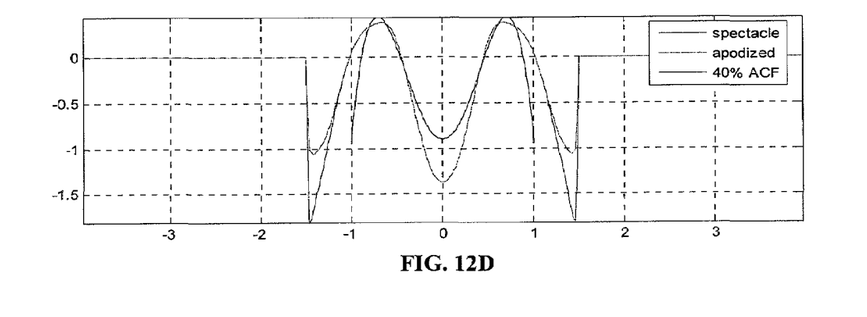

In a specific embodiment of the subject invention, the desired final programmed size can be determined and the information describing the eye aberration can be projected into a larger "transition" radius. FIG. 9 shows an example of the pupil region and the transition region. Preferably, the extrapolation is continuous while decaying toward zero. Alternatively, these can be achieved after the optimization.

Optimizing with respect to rotation and decentration can be performed independently. They may be done in either order depending on the expectation of the physical behavior, yielding results that may not be exactly the same depending on the rotational symmetry of the decentration range.

In an embodiment, the transition region may be de-emphasized by applying a decaying anodization. Further, the entire image may be refit with Zernike polynomials.

T All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

The invention claimed is:

1. A method for determining a lens wavefront, comprising:
measuring a patient's wavefront to create a pupil aberration p (n, m);

$$n, m = -\frac{L}{2}, \ldots, \frac{L}{2},$$

wherein the pupil aberration p (n, m) is represented on a grid, where n, m are indices of matrix elements, and L is the total number of pixels on a side of the grid, generating a plurality of corrected wavefronts $a_{ij}$ (n, m); where i, j are indices of $i^{th}$ horizontal and $j^{th}$ vertical positions, wherein each corrected wavefront in the $i^{th}$ and $j^{th}$ position, $a_{ij}$ (n, m), is expressed as $a_{ij}$ (n, m) p (n, m)+s(n+i, m+j), where s(n+i, m+j) is a lens wavefront in the $(n+j)^{th}$ horizontal and $(m+j)^{th}$ vertical position, wherein the pupil aberration p(n, m) and the lens wavefront s(n+i, m+j) are represented on a grid and i represents the $i^{th}$ horizontal position and j represents the $j^{th}$ vertical position on the grid;

generating a function of the plurality of corrected wavefronts $a_{ij}$;

determining a lens wavefront by optimizing the function of the plurality of corrected wavefronts $a_{ij}$; and producing a lens taking into account the lens wavefront.

2. The method according to claim 1, wherein generating the function of the plurality of corrected wavefronts $a_{ij}$ comprises computing orthogonal components of $a_{ij}$ for a pupil centered at a specific point of the lens wavefront for each combination of the $i^{th}$ horizontal position on the grid and the $j^{th}$ vertical position on the grid.

3. The method according to claim 2, wherein computing orthogonal components of $a_{ij}$ (n, m) comprises computing the inner product of $a_{ij}$ (n, m) with a set of orthogonal functions centered at a point of interest on the grid.

4. The method according to claim 2, wherein computing orthogonal components of $a_{ij}$ (n, m) comprises convolving $a_{ij}$ (n,m) with a set of orthogonal functions centered at a point of interest on the grid.

5. The method according to claim 1, wherein producing the lens further comprises fitting the lens wavefront across the lens.

6. The method according to claim 1, wherein the grid is an 8×8 grid and a pupil is represented as a 3×3 subgrid within the 8×8 grid.

7. The method according to claim 3, wherein the set of orthogonal functions are represented as approximations of Zernike polynomials.

* * * * *